United States Patent
Maget

[11] Patent Number: 5,928,194
[45] Date of Patent: Jul. 27, 1999

[54] SELF-CONTAINED LIQUID MICRODISPENSER

[76] Inventor: Henri J. R. Maget, 2661 Palomino Cir., La Jolla, Calif. 92037

[21] Appl. No.: 09/121,409

[22] Filed: Jul. 23, 1998

Related U.S. Application Data

[63] Continuation of application No. 08/833,530, Apr. 7, 1997, abandoned.
[51] Int. Cl.$^6$ .................................................. A61M 37/00
[52] U.S. Cl. .......................... 604/141; 604/131; 604/151; 604/49; 604/51; 604/890.1
[58] Field of Search ................................ 604/131, 890.1, 604/19, 23, 26, 48, 49, 51, 93, 140, 141, 143, 145, 151, 209, 310; 222/309

[56] References Cited

U.S. PATENT DOCUMENTS

| | | |
|---|---|---|
| 4,734,092 | 3/1988 | Millerd . |
| 4,902,278 | 2/1990 | Maget et al. . |
| 5,242,565 | 9/1993 | Winsel . |

*Primary Examiner*—Wynn Wood Coggins
*Assistant Examiner*—N. Kent Gring
*Attorney, Agent, or Firm*—Brown, Martin, Haller & McClain, LLP

[57] ABSTRACT

A compact, small, self-contained liquid containment and dispensing device is disclosed which included an elongated fluid reservoir/conduit, a liquid dispenser in the form of a liquid retentive matrix material, a gas pump and an electric pump activation circuit. The liquid to be administered or dispensed (e.g., a medication or fragrance vapor) is placed in the reservoir and the pump is activated, generating gas into the reservoir to expel the liquid from the reservoir to the matrix material at a controlled and essentially constant rate. Methods of use of the device to administer medications, provide vapors, and for other purposes are also disclosed. A substance to be administered (e.g., a medication or drug) which is soluble in the liquid can also be preloaded into the matrix material and administered by dissolution in the liquid. The device is sufficiently small to be easily portable and can be easily attached to a person's or animal's body for administration of medication to a human or animal patient. The devices may also be used, for instance, to dispense chemicals, vapor forming liquids, topical parasiticidal liquids, insecticide vapors, human or animal hormones, birth control compositions or antibiotics. The devices can be housed in compact but rugged housings which will stand up to the active movements of people or animals, or in decorative housings which can be used and displayed in homes, offices and other living or working areas.

37 Claims, 4 Drawing Sheets

SELF-CONTAINED LIQUID MICRODISPENSER

CROSS-REFERENCE TO RELATED APPLICATION

This application is a continuation of application Ser. No. 08/833,530, filed Apr. 7, 1997, of like title now abandoned.

BACKGROUND OF THE INVENTION

1. Field of the Invention

The invention herein relates to devices for dispensing of liquids, typically medications, fragrance-producing liquids or liquids producing desired vapors, in a controlled manner. More particularly it relates to portable, self-contained liquid dispensing devices which can dispense minute controlled quantities of liquids over a prolonged period.

2. Description of the Prior Art

In recent years there has been a substantial growth in the field of devices which are intended to dispense small amounts of liquids over an extended period of time at closely controlled low flow rates. While such devices have found uses in many field, they have been particularly valuable in the field of medicine and pharmaceuticals. In-patient treatment methods which rely on medications administered by such devices have proved quite successful for many diseases and dysfunctions. (For brevity, in much of the following discussion, the prior art devices and the devices of this invention will be exemplified for use in liquid medication dispensing. It is to be remembered, however, that the devices are usually equally functional for dispensing of other liquids, as will also be described below.) Many medical treatment protocols require slow administration of medications over prolonged periods, such as days or weeks, during which time it is undesirable to require a patient to remain confined to a medical facility in order to be properly medicated. Therefore small self-contained portable delivery devices that the patient can have implanted, carry or wear while going about his or her normal daily routine have been developed for use in such protocols. These devices are a necessity for successful out-patient treatment, treatment of long-term chronic conditions or in the convalescent stage of treatment following trauma, surgery or acute illness. These devices provide slow administration of medications over an extended time in the patient's home or otherwise away from a medical facility, in a setting in which the patient can be unrestricted in his or her movements.

There have been a number of different kinds of self-contained dispensing devices put into the marketplace. All require three components for successful operation. There must be a reservoir for the medication, a transfer component such as a medication-permeable film attached to the reservoir to serve as a conduit for the medication from the reservoir into the patient's body, and some sort of motivating force to cause the medication to move from the reservoir through the transfer component to the patient. The most common transfer component is a needle or cannula used to inject medication subcutaneously into the patient's veins, arteries, muscle or tissue. However, most recent research and development work has focused on the use of less invasive transfer components such as patches for transdermal administration, which require new types of motivating devices.

Various kinds of motivating devices have been described. There are passive pumping technologies such as osmotic devices and controlled or sustained release devices. The osmotic devices require a source of aqueous fluid such as water or aqueous body fluids. The motivating fluid must be in at least as great a volume as the fluid to be dispensed, since the devices work by fluid exchange. The controlled release devices are based on diffusional pressures through membrane barriers and require special formulations for the medication and the membranes in order to function properly.

Gas pressure devices for moving fluid have also been developed. Most have used gas evolution from a gas generating material to apply pressure to a flexible gas/liquid barrier, such as a rubber sheet. The expanding gas then presses against the flexible barrier and forces the liquid out of the adjacent liquid chamber and through the administration component. Gas generation in these kinds of devices commonly is obtained by reacting two chemicals together with one of the reaction products being the desired gas, or by dissolving a gas-containing material in a solvent such as water to cause evolution of the gas. There are severe limitations on these types of devices, however, since there are only a limited number of chemicals which when reacted in small quantities will generate sufficient gas to be a driving force in a dispensing device, or which can be dissolved to form such a quantity of gas. Moreover, such devices are necessarily further limited as to the gas itself which may be used and to the potential chemical reactants for production of the gas. The devices must involved use only those gases and gas generating chemicals which are safe, non-toxic and non-allergenic for the patient, which can be easily and properly handled and which are compatible with the other components of the device, particularly the gas/liquid barrier.

Further, and most importantly, these devices are limited in the time period over which they will operate, since gas generation or evolution is a relatively rapid phenomenon and ceases as soon as the reactant chemicals are fully reacted or the soluble material is fully dissolved. Thus, while the gas pressure will be high early on, as the device continues in use over a period of time the gas pressure will fall and the ability of the device to dispense the medication fully at an accurate and desired flowrate will diminish. Such devices therefore find their greatest use in treatment regimens where the medication in the device is to be administered to the patient over a relatively short time, such as a few hours or days.

Another type of gas generating device has much greater flexibility and ability to be used for sustained administration of medications. These are the devices that depend upon electrochemical pumps to move the liquid through the dispensing device and into the patient. I have previously developed a number of electrochemical pumps as well as the drug dispensing devices which utilize such pumps as the motivating force. A particularly relevant previous device which I developed is illustrated in my U.S. Pat. No. 4,902,278 entitled "Fluid Delivery Micropump" (issued in 1990). This patent describes a electrochemical prime mover module for use in fluid delivery micropump (especially for pharmaceutical purposes) which uses an ion exchange cell in which water is reduced and pure oxygen regenerated to apply external gas pressure to a collapsible reservoir and expel a fluid from the reservoir. (As will be evident from the description below, the prime mover described in that patent is also an important element in the present device.)

Another prior art device relevant to the present invention is described in U.S. Pat. No. 4,734,092 to Millerd (issued in 1988). Millerd describes a device to inject a drug into the human body with a needle via intravenous, intraarterial, intramuscular and subcutaneous routes.

Some of the prior devices, including mine, have been commercially successful in various settings. However, no one has yet been able to provide an effective micropump with a direct gas-liquid interface in which the interfacial surface area is sufficiently small to reduce problems such as gas dissolution in the liquid and interphase contamination to an insignificant level, while simultaneously being able to steadily and accurately transfer the fluid to a porous surface from which it can be removed by evaporation or diffusion.

SUMMARY OF THE INVENTION

The present invention overcomes the deficiencies of the prior art. It provides a simple, economical, compact liquid dispensing device which can store within itself sufficient liquid to operate for long periods of time and yet maintain a closely controlled flow rate with only a small range of variation during use of the device. In many cases, the flow rate remains substantially constant over most of the operational life of the device.

A principal use of the device is for dispensing or administering a liquid medication or other agent intended to produce a physiological effect in a recipient human or animal. The device is sufficiently small to be easily portable and can be attached to a person's or animal's body in an unobtrusive location where there is no discomfort or inconvenience to the patient. Numerous liquid materials, not limited only to medications, may be administered to humans or animals by the device. Typical examples include, but are not limited to, liquids which are or contain human or animal hormones, birth control compositions, motion sickness medications, antibiotics and many other useful compositions.

In addition to use for dispensing liquid agents to a human or animal subject or patient, the devices of this invention may also be used to dispense liquid chemicals, vapor forming liquids and their resulting vapors; as air freshening devices; and for dispensing of other liquids to deal with specific problems, such as topical liquids to kill parasites on the surface of a human or animal patient or insecticide vapors, insect attractants or pheromones.

The devices can be housed in compact but rugged housings which will stand up to the active movements of people or animals, or in less rugged but more decorative housings which can be used and displayed in homes, offices and other living or working areas.

In preferred embodiments, the electrical components are completely enclosed in their own housing so that the device can be made weather and environment resistant for use out of doors in inclement weather.

Among the materials which may be provided or administered are medications, hormones, drugs, other treating agents for disease or dysfunction, vitamins, minerals, dietary supplements, biological compositions, fragrances, insecticides, insect attractants, pheromones or vaporizable compounds which mask or eliminate undesirable odors in the ambient environment.

In a broad embodiment, the invention is of a self-contained liquid containment and dispensing device which comprises an elongated fluid conduit having a first end and a second end and an internal volume sufficient to contain a predetermined quantity of liquid; a liquid dispenser in fluid communication with the first end of the conduit; a gas generation member in fluid communication with the second end of the conduit for generating gas and pumping the gas into the conduit through the second end; and an activation circuit comprising an electric power source for electrically activating the gas generation member; whereby when liquid is contained in the conduit and the gas generation member is activated to generate and pump the gas into the second end of the conduit, the pumped gas forces the liquid to be expelled from the conduit through the first end onto an absorption or collection pad adjacent thereto and dispensed though the absorption or collection pad.

The invention also includes methods of use of the devices to administer medications, provide vapors, and for other fluid flow and fluid administration purposes. Therefore, in another embodiment the invention is of a method of administering a liquid (which may be a pure liquid or a liquid solution) to a human or animal subject which comprises providing a self-contained liquid containment and dispensing device which comprises an elongated fluid conduit having a first end and a second end and an internal volume sufficient to contain a predetermined quantity of liquid; a liquid dispenser comprising an absorption or collection pad adjacent to and disposed to receive liquid from the first end of the conduit; a gas generation member in fluid communication with the second end of the conduit for generating and pumping gas into the conduit through the second end; and an activation circuit comprising an electric power source for electrically activating the gas generation member; placing a quantity of the liquid within the conduit; attaching the device to the patient or object in such manner that the pad is in fluid communication with the patient or the air environment; and activating the circuit to operate the gas generation member to generate and pump the gas into the second end of the conduit, the pumped gas forcing the liquid to be expelled from the conduit through the first end and administered or dispensed though the pad in contact with the patient or the environment.

In yet another embodiment, the invention involves a method of delivering a vaporized liquid to the ambient environment which comprises providing a self-contained liquid containment and dispensing device which comprises an elongated fluid conduit having a first end and a second end and an internal volume sufficient to contain a predetermined quantity of liquid; a liquid dispenser comprising an absorption or collection pad adjacent to and disposed to receive liquid from the first end of the conduit; a gas generation member in fluid communication with the second end of the conduit for pumping gas into the conduit through the second end; and an activation circuit comprising an electric power source for electrically activating the gas generation member; placing a quantity of volatile liquid within the conduit; in the conduit; placing the device containing the volatile liquid within the ambient environment; and activating the circuit to operate the gas generation member to pump the gas into the second end of the conduit, the pumped gas forcing the liquid to be expelled from the conduit through the first end to the pad; retaining at least a portion of the volatile liquid within the pad for a period of time sufficient for the portion to vaporize; and dispersing the resultant vapor through the pad into the ambient environment.

Details of the various embodiments will be set forth below.

DETAILED DESCRIPTION AND PREFERRED EMBODIMENTS

A device of the present invention provides a compact easily used and accurate liquid dispensing device whose unique capabilities result from the combination of a proven and highly efficient pump, a reservoir or maintenance retention chamber in a form in which the gas pressure produced by the pump acts on only an extremely small portion of the surface of the liquid to be dispensed, and an integrated dispensing member which can deliver the liquid as, for instance, a transdermally administered medication, as a vapor, or for topical or other applications.

The device is best understood by reference to the drawings. Considering first the embodiment of FIGS. 1 and 2, the device 2 contains a pumping module 4, a reservoir or retention chamber 6 in the form of a flat spiral-coiled conduit formed of tubing 8, and a dispensing member 10. The dispensing member contains a porous liquid dispersion pad 5 which is positioned below the outlet of the chamber 6. In one embodiment shown in FIGS. 1 and 2, outlet end 1 6 of tubing 8 has attached in fluid communication an open needle or cannula 7 which extends into dispensing member 10. The cannula 7 has a beveled tip 9 to cause increments of the exiting liquid to form as individual drops, which fall from the cannula tip 9 onto the pad 5 and are dispersed throughout the pad. If the tubing 8 is made of a sufficiently rigid material, the tubing itself may extend into dispensing member 10 in place of the needle or cannula 7, and have its outlet end 16 beveled as at 9'.

The pumping module 4 will often be referred to simply as a pump and will be described in more detail below. It is substantially equivalent in structure and function to the prime mover module described in my aforementioned U.S. Pat. No. 4,902,278. It is operably connected by fluid communication connection 12 to the inlet end 14 of the spiral coil 8. Gas generated by the pump 4 flows into the inlet 14 of coil 8 and forms a gas/liquid interface 20 (see FIG. 3) with the fluid 22 to be dispensed filling the downstream portion of the tubing 8.

Figures 1, 2, 3:
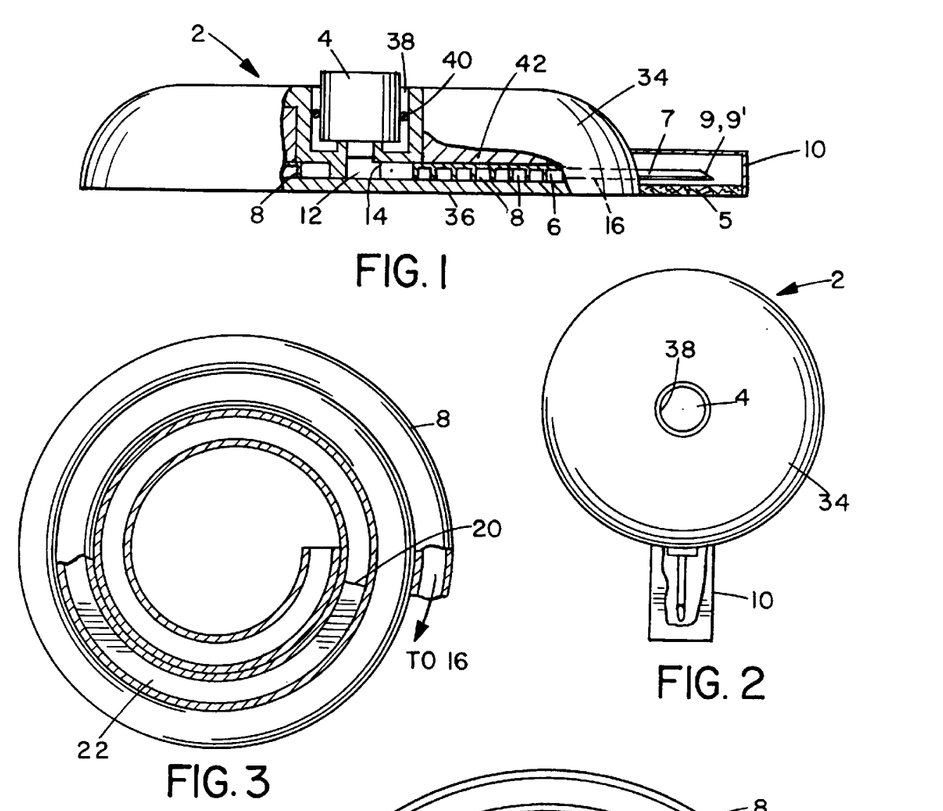
FIG. 1 is a side elevation view, partially in section, of one embodiment of the present device, the embodiment having a flat, spiral shaped liquid containment chamber.
FIG. 2 is a top plan view of the device of FIG. 1.
FIG. 3 is a top plan view of the central inlet portion of the flat, spiral shaped liquid containment chamber of the device of FIG. 1.
Figure 9:
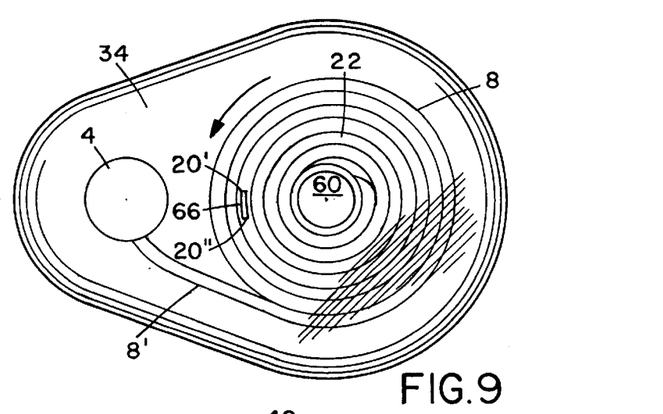

It will be understood that the gas/liquid interface 20 is a moving interface which progresses down the tubing 8 from a point in the direction of the inlet end 14 toward the outlet end 16, as illustrated in FIGS. 3 and 9. The exact location of the interface 20 at any given time will of course be dependent upon the amount of liquid remaining in the tubing 8. As will be discussed below, there may be plurality of liquids traversing tubing 8 simultaneously for seriatim dispensing, with each adjacent pair of liquids being separated by a suitable separation material, with a single gas/liquid interface 20 at the upstream end of the last liquid.

For brevity herein, the presence of the gas/liquid interface 20 and the liquid content 22 are partially illustrated schematically in FIGS. 3 and 9. Except where the aspects of the interface and gas or liquid contents need to be specifically described further, these will not be illustrated in the succeeding Figures, but those skilled in the art will of course understand that the gas and liquid content and the interface between the two phases will be present in all of the devices in their operating modes.

In the embodiment of FIGS. 1 and 2, the product is formed in the shape of a relatively thin flat circular device encased in a housing 34 overlaying a base 36. The housing 34 contains a well 38 to receive the pump 4, which is retained in place by an O-ring seal 40 which prevents escape of the generated gas from the unit, so that all the gas passes into the reservoir conduit 8. Most of the interior of the housing 34 may conveniently be filled with a spacing or filler material 42 which is conveniently a polymeric or elastomeric foam. The top of housing 34 can be molded with the spacing material 42 adhered in place or simply incorporated as part of the housing 34. The purpose of the spacing material 42 is to provide thermal insulation to the conduit 8 and also to provide sealing when the chamber 6 is of the open conduit concentric circular configuration of FIGS. 4 and 5. If the pump 4 is not completely self-contained the housing 34 may also contain space to hold components of the pump. Spacing material 42 need not be continuous as illustrated, but may also be in the form of a plurality of ribs formed on the underside of the top of housing 34 in sufficient quantity to maintain the device's components in position.

Figure 4:
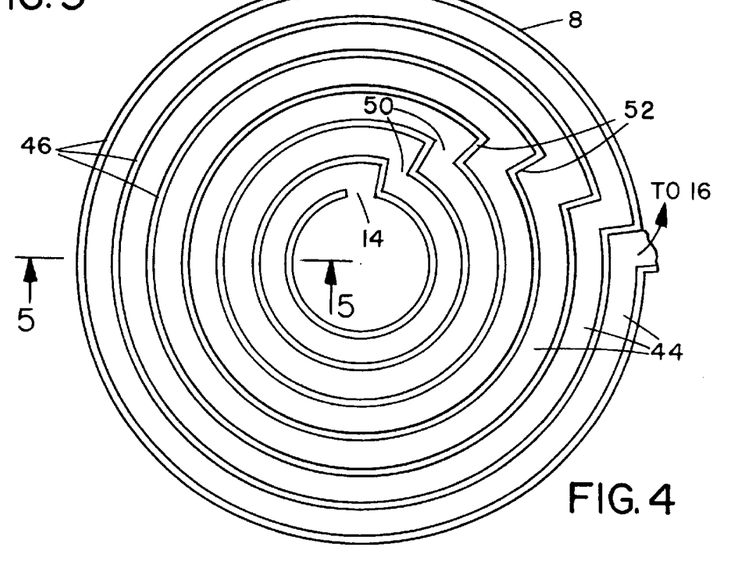
FIG. 4 is a top plan view of the central inlet portion of an alternative liquid containment chamber for the device of FIG. 1, in which the liquid containment chamber is formed of concentric circular conduits, and illustrating the fluid communication connections between adjacent concentric circular conduits which enable the contained liquid and motivating gas to move to the outlet of the chamber.
Figure 5:
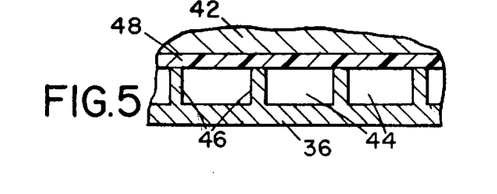
FIG. 5 is a fragmentary cross-sectional view taken on Line 5—5 of FIG. 4, illustrating the fluid flow conduits and means for sealing the conduits against crossover or overflow.

The principal types of conduits 8 of the present invention are illustrated in FIGS. 3–5. Chamber 6 consists of a continuous spiral flow fluid path which is formed by creating a flat spiral coil of tubing 8, which will be held in place by spacer material 42. Different volumes of chamber 6 can be obtained merely by selecting different lengths and inside diameters of tubing 8.

FIGS. 4 and 5 show an alternate flow path configuration, which consists of a series of concentric adjacent circular channels 44. The channels are formed by concentric ring walls 46, originating at inlet end 14 and providing a fluid flow path to outlet end 16. The channels 44 are formed by the concentric walls 46, barrier walls 52 and base 36. For manufacturing purposes, these may be formed as a single molded piece. The spacing material or ribs 42 rest against a gasket or seal 48, which is commonly of rubber or some other elastomeric material. Assembly of the device 2 then results in the seal 48 being seated along the top of each of the ring walls 46, thus isolating each of the concentric channels 44 from its adjacent neighbors. As noted above, if the spacer material itself has sealing properties, it may be used in place of gasket 48, although use of gasket 48 is preferred.

Fluid communication between the sealed adjacent channels 44 is obtained by a series of apertures 50 between adjacent channels. Each channel 44 has two such apertures, opening respectively to the next outwardly and inwardly adjacent channels. Preferably these two apertures 50 are closely adjacent to each other and separated only by barrier wall 52, such that fluid flowing into the aperture opening from the next outward conduit makes an entire circuit around the length of the circular channel 44 and exits from that channel through the next aperture 50 into the next inwardly adjacent channel 44, with the barrier walls 52 preventing the fluid from bypassing any part of the path. Both the liquid and the motivating gas thus move generally outwardly from the inlet end 14 of the reservoir conduit 8 to exit at the outlet 16 and the dispersing device 10.

It will be recognized that the configuration of adjacent concentric channels 44 shown in FIG. 4 need not be circular. Rather if desired the chamber 6 flow path could be molded in the form of concentric triangular, square, pentagonal, hexagonal, or other polygonal shapes. These are less preferred than a circular shape, since in addition to the flow direction changes for the liquid at each of the barrier walls 52 to pass through the apertures 50, the polygonal shapes also impose abrupt fluid flow direction changes at each of the vertices of the polygon. Of course, the more sides that the polygon has, the less abrupt each of the flow changes at the vertices will be, since these higher polygons essentially approach circular in shape. The lateral cross-section shape of the channels 44 will preferably be substantially square or rectangular as shown in FIG. 5, with optionally coving or fillets on the inside corners to facilitate fluid flow. Other shapes, such as semicircular, semioval or semielliptical are also possible.

Various types of common tubing can be employed for the spiral shaped liquid container 6 embodiments, depending on the nature of the liquid and gas. Typically the tubing may be of polyethylene, polypropylene, polytetrafluoroethylene (e.g., Teflon™), or other polymers which are chemically inert to the fluid materials and are sufficiently transparent or translucent that the progress of the liquid flow can be observed. Glass tubing is also suitable, and is preferred for those fluids (such as many pharmaceuticals) which are unstable when in contact with organic (polymeric) surfaces. While metal tubing could be used, it is not preferred, since it is usually more expensive, harder to fabricate into small size coils, prone to rupture upon impact, and, most importantly, opaque so that liquid flow cannot be observed.

Other configurations of the invention will be evident from subsequent Figures. In FIGS. 6–9, another flat configuration is shown in which the pump 4 in well 38 in housing 34 is separated from the fluid delivery unit 60 housed in well 56 in the housing top 34. The dispensing unit 10 is in the form of an evaporation pad 68 or transdermal pad 57.

Figure 7:
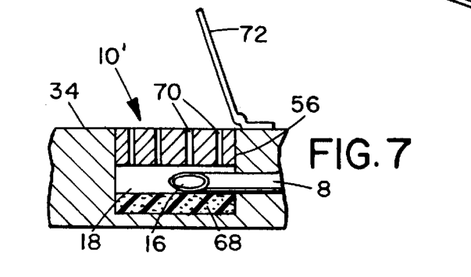
FIG. 7 is a partial sectional elevation view of another embodiment of that portion of the device of FIG. 6 designated as area A.
Figure 8:
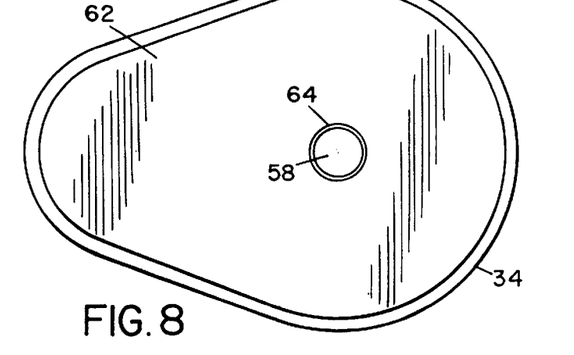
FIGS. 8 and 9 are respectively bottom and top plan views of the device of FIG. 6, with FIG. 9 also showing progress of a fluid through the device.

When used for evaporation of a liquid, the dispensing member 10' includes evaporation pad 68 seated in the well 56, as indicated in FIG. 7. This configuration is particularly useful when the liquid is intended to be vaporized to provide a vapor which imparts a fragrance, provides an air cleaning or insect repellent function, or provides another function for which vapors may be used. In the embodiment shown in FIG. 7, the liquid exiting outlet port 16 of conduit 8 into space 18 drips or otherwise flows onto evaporation pad 68 and disperses throughout the pad. The liquid will have sufficient volatility to vaporize when dispersed in the pad, such that the vapors pass upward and through outlet channels 70 and enter the ambient atmosphere. Depending on the liquid being used, the resulting vapors being dispersed from the device 2 can provide a pleasing fragrance (such as the fragrance of pine trees, flowers, etc.), serve as an air freshening or odor masking vapor, or disperse an insecticide into the ambient air. Volatile liquids which perform these functions are well known and readily available. The vapor dispensing capability thus provides for the device to serve as a room air freshener or odor remover and the housing 34 can be formed in an attractively designed shape (such as the pear shape shown in FIGS. 8 and 9) and attractively finished on the surface, as with pictures of flowers, trees, attractive color patterns, and the like to enhance the appearance for use in residences, offices and so forth. It may also be desirable to attach a cap 72 to be able to open and close access to dispensing unit 10' as needed, and have a similar cap (not shown) covering pump 4. Thus, when pump 4 is turned off (using circuitry such as described below) no fragrance or other vapor is emitted from dispensing unit 10'. This permits one to selectively turn on or off the vapor dispensing device as desired.

Figure 6:
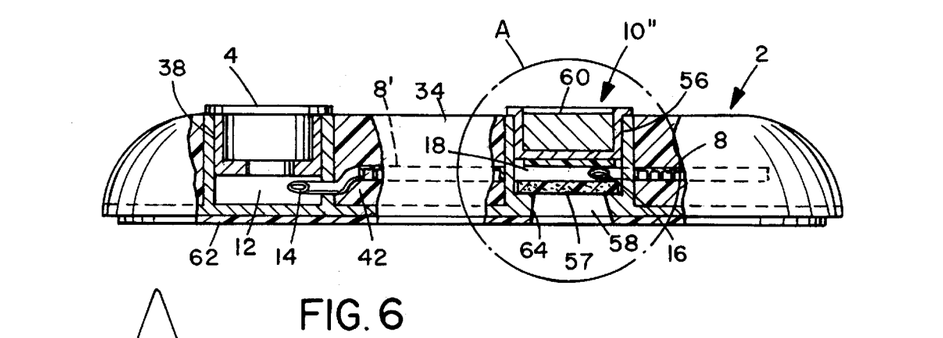
FIG. 6 is a side elevation view, partially in section, of another embodiment of the present device.
Figure 11:
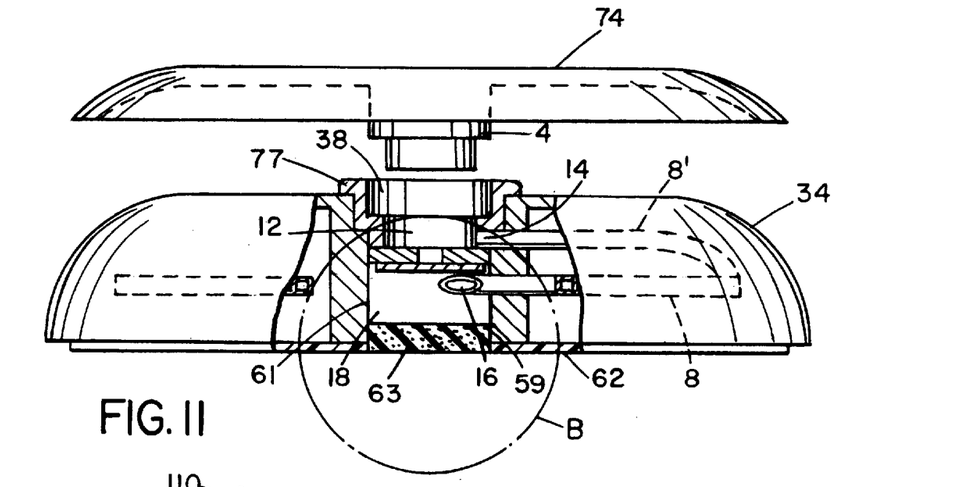
FIG. 11 is a side elevation view of another embodiment of the present device, illustrating a removable and reusable energy module component.

In the embodiment shown in FIG. 6, evaporation pad 68 is replaced by transdermal pad 57, well 56 has an opening 58 through base 62, and is closed at the top by plug 60. Pad 57 is supported by shoulder 64 formed in the wall of well 56. As the liquid exits from the outlet 16 of tubing 8, it drips onto pad 57 and disperses through the pad. As the pad becomes saturated either locally or entirely, the dispersed liquid forms drops and falls through opening 58 onto the skin of the patient to which the device 2 is attached. This configuration is useful, for instance, when the patient has an open wound into which medication is to be administered, but it is desired to avoid any contact by pad 57 with the wound. The device would be sized with opening 58 surrounding but not touching the wound, with the liquid then dropping from pad 57 directly into the wound. (An alternative configuration, with a transdermal pad positioned for direct contact with the patient's skin, is illustrated in FIG. 11.)

Flow of fluid through a device of the present invention is illustrated in FIG. 9, in which an embodiment with a transparent housing 34 and transparent conduit 8 is illustrated. If the fluid 22 is colored, either naturally or by addition of a coloring agent such as a food colorant, its progress ahead of gas/liquid interface 20 can be easily monitored. Similarly, but less commonly, if the motivating gas is colored, the interface 20 will also be visible and the progress of the liquid, even though colorless, can be monitored. In the event that both liquid and gas are colorless, one can insert a colored liquid slug 66 at the upstream end of liquid column, so that there is a liquid/liquid interface 20' between the dispensant liquid 22 and the slug 66 and a gas/liquid interface 20 between the motivating gas and the slug 66. The slug is conveniently formed of a liquid which has a high degree of surface tension and is not miscible with the liquid 22, so that the slug 66 will remain as a separate unit and will not mix with the liquid 22 or disperse into the upstream gas section of the conduit 8. However, the slug must not be formed of a material which is unduly viscous, since its progress through the conduit 8 will then be impeded and the dispensing rate of the liquid 22 will be adversely affected. Similarly, the slug 22 composition must be such that it is chemically inert to the material of conduit 8, the liquid 22 and the motivating gas, and, if the liquid 22 is a medication to be administered to a human or animal patient, it must also be physiologically inert to that patient. There are a number of light oils, including hydrocarbon, silicone and fluorocarbon oils, which have appropriate surface tension, viscosity and compatibility properties to be used as the slug 66.

The non-miscible fluid "slugs" may also have functional uses other than merely as liquid/liquid or liquid gas separators or visual markers. For instance, when the device is intended for dispensing of insecticides, a slug composed of an insect attractant chemical could precede an insecticide liquid.

Use of one or more slugs 66 also permits moving two or more liquids 22 through the device simultaneously. A first slug 66 would follow the first liquid 22 and in turn be followed by a second liquid, so that the first slug 66 would have liquid/liquid interfaces at both of its ends. The second liquid could be followed directly by the motivating gas, or by a second slug, with either the gas following the slug, or a third liquid following the slug. The various liquids would thereby be dispensed seriatim. Of course when any one or more slugs are used, the system must be monitored to see that the slug material is appropriately disposed of, unless it too can be vaporized, administered to a patient, or otherwise treated like the liquid 22.

Figure 10:
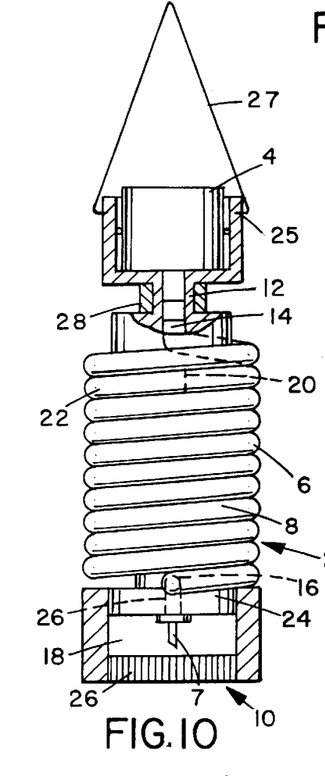
FIG. 10 is a side elevation view of another embodiment of the present invention, disposed in a vertical position and having a helical-coil shaped liquid containment chamber.

In the embodiment shown in FIG. 10, a chamber 6 in the form of helically-wound tubing 8 is wound around an inert cylindrical support 24 for strength and to avoid breakage. This core will preferably be a piece of plastic or a polymeric foam material, which may be formed by molding, thermoforming and bonding, or other conventional forming processes. Other materials such as wood, rubber or metal may be used, but are generally more expensive and more difficult to fabricate. The core 24 will have passages 26 and 28 cut through portions of it to provide for fluid connection of the respective ends of the tubing 8, the pump 4 and, if needed, a cannula 7 into the dispensing member 10. The device illustrated in FIG. 7 is intended to be used in the vertical position, with pump 4 located either up or down. By selecting a cannula 7 or similar component, such as small bore tubing, having a resistance to flow, the liquid 22 can be maintained in the helical coil reservoir 6 capped by pump 4. Liquid flow will occur as soon as the gas pressure generated by the pump 4 overcomes this resistance. Cannula 7 allows fluid to drop onto absorption pad 21 in chamber 18 from which it can evaporate into the air. The device 2 is provided with a wire hook 27 attached to a casing 25, for hanging the device from a convenient hook (not shown).

Another embodiment is shown in FIG. 11 in which a separate top portion 74 contains the pump 4 and is molded or otherwise shaped to fit over the housing 34 with the pump 4 being seated in recess 38 and held in place with vapor or gas seal 77 to ensure good fluid and gas contact through inlet area 12 to inlet end 14 of conduit 8 (in this case through extension 8'). The pumped liquid then flows out of outlet 16 in space 18 and drips onto a transdermal or other dispensing pad 63, which is mounted within the lower portion of well 61 and extends into a cutout portion 59 of base 62. Base 62 may also be or be coated with an adhesive composition, for adherence of the device to the skin of a patient, when the device of FIG. 11 is to be used to administer medication topically or transdermally from pad 63 to the patient.

This embodiment is particular suited for an alternative form of transdermal drug delivery. The pad 63 is preformed with an embedded content of a soluble drug, The liquid 22 (e.g., water, lipid) delivered by the conduit 8 will be a solvent for the drug in the pad 63 matrix, which dissolves the drug and then maintains a high dissolved drug concentration, and thus high transfer gradient, throughout the matrix or adhesive. This in turn allows the entire quantity of drug to reach the skin interface, regardless of the original distance of any specific portion of the drug from that interface. This results in improved stability of the interfacial concentration of the drug and therefore stability of the transdermal transfer rate and also in substantially complete utilization of the drug.

Figure 15:
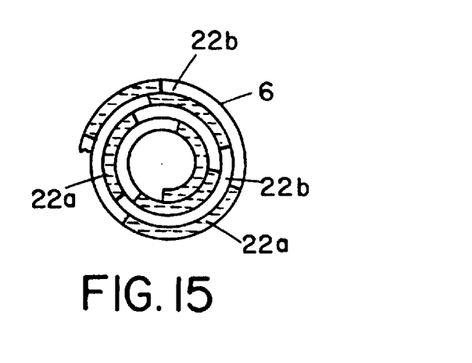
FIG. 15 is a schematic diagram related to FIG. 9 and depicting graphically the use of alternating liquids in the reservoir to control the time and duration of transdermal delivery of a drug.
Figure 16:
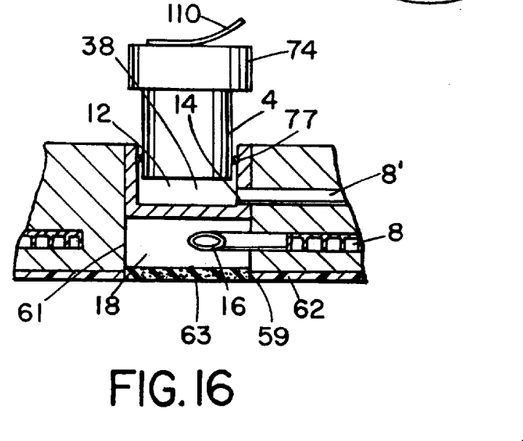
FIG. 16 is a partial sectional elevation view of another embodiment of the portion of the device of FIG. 11 designated as area B.

In a related embodiment, the conduit 8 may be filled with both a drug solvent fluid 22a and a fluid 22b inert to the drug, which would be placed in the conduit 8 in separate predetermined quantities along the length of the conduit 8, as indicated graphically in FIG. 15. As the fluid segments 22a and 22b exit seriatim from the conduit 8, the drug is alternately transported toward the skin interface (when the solvent fluid 22a is present) and held in the pad matrix 63 (when the inert fluid 22b is present). By appropriate proportioning of the fluid segments 22a and 22b in the conduit 8 and control of the rate of fluid flow, a punctuated program of transdermal drug delivery can be maintained, which can emulate various body cycles (e.g., the circadian cycle) and thus optimize the time of delivery of the drug. A typical combination of fluids would be water and lipid, for water-soluble drugs.

This embodiment may be described as "semi-disposable," since the top portion 74 with the pump 4 and its associated battery 76 can be removed as a unit from a device from which the fluid has been exhausted, and can then be re-attached to a different reservoir which is completely or partially full of fluid. It is typical for the battery 76 to be capable of running for a substantially longer time than it takes to pump out all of the liquid from a single device. Thus section 74 can subsequently be reused until the battery power has been exhausted. Moreover, the battery 76 itself can be replaced so that the section 74 can be moved from unit to unit and with periodic battery replacement be used for an extended period of time with a large number of different individual vapor or liquid dispensing devices.

This embodiment is an improvement over prior art devices in which the driving mechanism for transdermal drug delivery was the concentration gradient between the drug in the matrix or adhesive and the skin. Initially such gradient is large, but decreases progressively as the drug is used and depleted. The rate of change is dependent upon the geometry of the system; i.e. the transfer surface area (which should be large) and the matrix or adhesive thickness (which should be small). However, as that portion of the drug which is close to the skin interface is depleted, the remaining quantity of the drug further back in the matrix or adhesive is not effectively transported to the skin interface, resulting in significant underutilization of the overall drug content of the prior art device.

Figure 12:
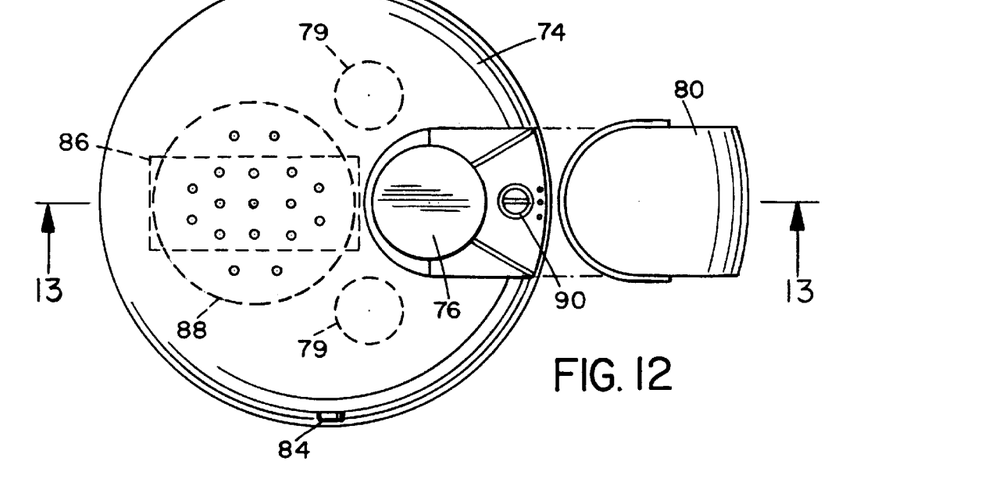
FIGS. 12 and 13 are respectively a top plan view and a centerline sectional elevation view of the device of FIG. 11, illustrating typical positions of the electrical components of the energy module and means for access to the replaceable battery.
Figure 13:
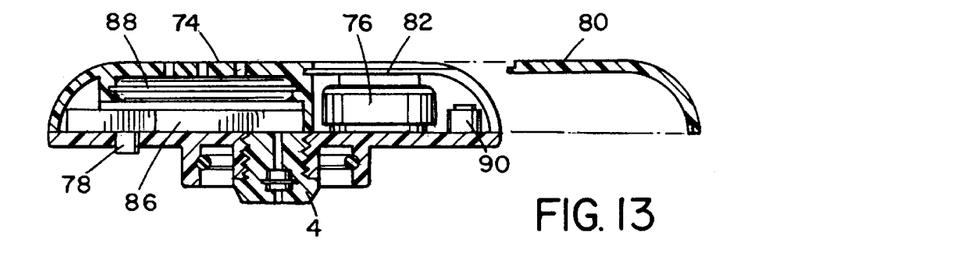

The utility of the removable cap or section 74 can be best understood by reference to FIGS. 12 and 13. The cap 74 is illustrated as including all of the electrical components necessary to run and control the pump 4, including battery 76 and an off/on switch 78. The off/on switch 78 may be a pressure switch so that pushing the cap 74 onto the housing 34 automatically causes the pump 4 to be activated. Removal of the cap 74 releases the pressure and allows the switch 78 to open so that the pump stops running. Access to the battery 76 is obtained through a removable cover 80 which slides into a receiving groove 82. Such removable covers are common for access to batteries in many types of devices.

Figure 14:
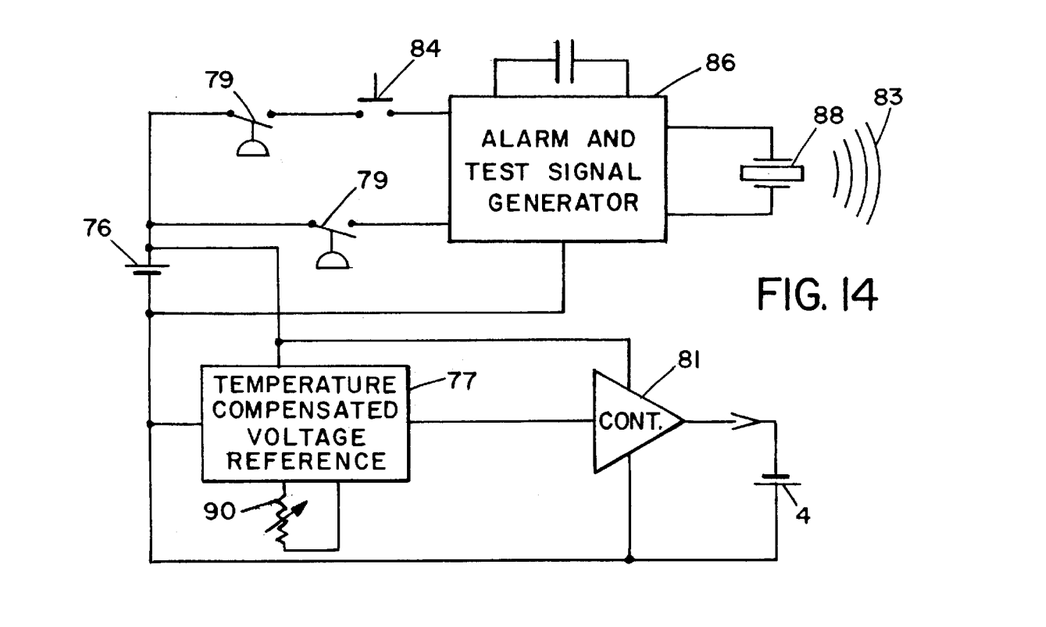
FIG. 14 is a schematic electrical wiring and component diagram illustrating typical electrical circuitry and components for use in the present invention.

Typical electrical circuitry is illustrated in FIG. 14. The electrochemical cell 4 is connected to the battery 76 in the circuit which includes a temperature compensated voltage reference 77 which is set by potentiometer 90, and current controller 81. Alarm-and-test-signal generator 86 is normally operated in response to signals from over- and under-pressure sensors 79, which are activated with the oxygen pressure in the chamber moves out of the desired range. The signal generator 86 can be tested by manual depression of switch 84. The signal generator 86 activates piezo-acoustic disk 88, which emits an audible signal 83 indicating an alarm condition resulting from the under- or over-pressures sensed by pressure sensors 79.

Figure 17:
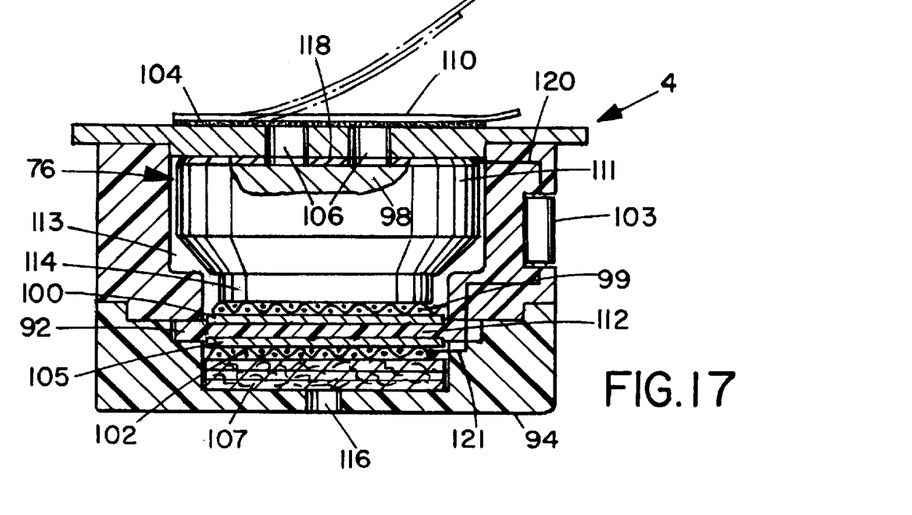
FIG. 17 is a schematic side elevation view of a pump module of this invention.

The pump 4, shown in FIG. 17, is constructed in the same manner as the prime mover modular unit described in the aforesaid U.S. Pat. No. 4,902,278. In this instance, the pump 4 includes battery 76 and an electrochemical cell 92, both disposed within pump housing 94.

The battery 76 has a casing 11 8 which surrounds a core 98 filled with a conventional power source material. The material undergoes a chemical reaction to convert chemical energy into electrical energy by processes well known in the art. The electrical energy produced by the source material is manifested as a voltage differential between the cathode 111 and anode 114 forming a part of the battery 76. The battery 76 can be one of various well known types of primary batteries, such as a mercury battery, manganese dioxide battery, aluminum-air battery or zinc-air battery. Air-actuated batteries, such as the aluminum-air battery or the zinc-air battery, or other batteries which produce power only when exposed to an activating agent, are preferred because they can be used without a mechanical or electrical on/off switch 84 in the prime mover circuit. The zinc-air battery is the preferred battery 76.

The battery 76/cell 92 circuit includes current collectors 99 and 102 and resistor 103, which regulates the current developed in the module. The electron current across the ion exchange mechanism causes the reduction/oxidation reactions to occur, which causes regeneration of oxygen gas at the regeneration electrode 105, the pressure of which causes the fluid to flow through the device. Hence, the rate of oxygen generation and thus the fluid delivery rate are fixed by the circuit resistance (if there is no resistor 103) or by the value of the resistor 103. For example, a prime mover module using a zinc-air battery (which produces a voltage of about 1.25–1.45V) and a resistor 103 of about 7000Ω can produce a fluid delivery rate of about 0.5 mL/day.

The pump 4 shown in FIG. 17 uses a fixed value resistor 103 to deliver fluid at a substantially constant flow rate (assuming the use of a substantially constant voltage battery). Resistor 103 is connected by wire 120 to battery cathode 111 and by wire 121 to cell anode collector 102. This type of pump is preferred for applications requiring a universal flow rate because it is simple to manufacture and easy to use. However, for applications requiring changeable flow rates, the fixed resistor 103 may be replaced by a variable resistor or potentiometer to provide means for varying the delivery rate of the pump 4.

The battery 76 applies a voltage across the electrochemical cell 92 by connection with the resistor 103. The cell 92 includes an ion exchange electrolytic membrane 112, preferably a perfluorosulfonic acid membrane coated with 90% platinum black/10% polytetrafluoroethylene, sandwiched between a pair of material-previous electrodes 100 and 105 and a pair of current collection screens 99 and 102, preferably titanium screens or porous titanium disks. Battery anode 114 and cell cathode/electrode 100 have a common in current collection screen 99. A particularly simple and compact structure is obtained by making one of the battery electrodes integral with one of the electrodes of the electrochemical cell. A water-moistened porous sponge 107 abuts the downstream side of screen 102 and serves as the water source for regeneration of the gaseous oxygen. In the preferred embodiment of the zinc-air battery, a pair of air inlet ports 106 formed in the wall 104 and casing 118 expose the battery core 98 to the ambient environment. Atmospheric air enters the ports 106 and reacts with the zinc in the core 98 to produce electrical energy in accordance with well known processes. To preserve the battery 76 when the pump is not in use, the ports 106 are sealed by a peelable protective tab 110, preferably adhesive tape, which is applied to the outer surface of the end wall 104 and extends across the ports 106. When the pump 4 is ready for use, the battery 76 is activated by peeling off the tab 110.

When the tab 110 is removed, the battery 76 is activated and atmospheric oxygen is drawn into the housing and reduced at the cathode of the electrochemical cell, thereby promoting the generation of oxygen from the water in sponge 107 on the other side of the electrochemical cell, or anode. The oxygen gas so formed passes through the cell exit port 116 to inlet port 14 into the conduit 8 or channels 44. The resulting increase of gas (oxygen) pressure in the inlet 14 acts against the liquid/gas interface 20 and urges liquid through the conduit 8 or chambers 44 and out of the conduit end 16 to the administration device 10 for infusion into the body of a patient under treatment, dispensing of vapor, etc.

Although the preferred start/stop mechanism for the battery 76 is the port 106/peelable tab 110 combination described above, another mechanism or structure capable of selectively exposing or sealing the battery core 98 from the battery activating agent can be used. Moreover, the ambient environment need not necessarily be atmospheric air but can be another open or closed environment containing an activating agent compatible with the battery used in the pump 4. It will also be apparent that the mechanical or electrical switch or similar on/off device 84 can also be present with the tab 110 and be used as a primary or secondary start/stop mechanism, with the tab 110 serving in the alternate capacity.

Details of the structure and function of the electrochemical cell are set out in my U.S. Pat. Nos. 4,402,317 and 4,522,698, both entitled "Electro-Chemical Prime Mover." The entire disclosures of those patents are incorporated herein by reference and thus need not be extensively repeated here. Suffice it to say that the voltage gradient established across the electrochemical cell reduces an electrochemically active material, such as the atmospheric oxygen entering the air inlet ports 106, at the electrode 100, consuming the protons generated at the counterelectrode 105 as a result of the oxidation of the water (available from cellulosic sponge 107) into oxygen evolved in the region adjacent to port 116. When the electrochemically active material is atmospheric oxygen or oxygen from some other source, the electrode 102 is conveniently called the oxygen evolution electrode.

The electrochemical behavior of the prime mover module and the interaction between the battery 76 and the electrochemical cell 92 is characterized by the following reactions:

$$\tfrac{1}{2}O_2 + H_2O + 2e^- \rightarrow 2OH^- \tag{1}$$

$$Zn + 2OH^- \rightarrow ZnO + H_2O + 2e^- \tag{2}$$

$$\tfrac{1}{2}O_2 + 2H^+ + 2e^- \rightarrow H_2O \tag{3}$$

$$\tfrac{1}{2}O_2 + 2H^+ + 2e^- \leftarrow H_2O \tag{4}$$

in which:

Reaction (1) occurs at the air cathode 111 of the battery.

Reaction (2) occurs at the zinc anode 114 of the battery.

Reaction (3) occurs at the interface between the electrolytic membrane 112 and the cathode 100.

Reaction (4) occurs at the interface between the electrolytic membrane 112 and the anode 105.

The overall behavior of the prime mover module can be described as the sum of the battery 76 and cell 92 reactions as follows:

$$\text{BATTERY: } \tfrac{1}{2}O_2(\text{Air}) + Zn \rightarrow ZnO + \text{energy} \tag{5}$$

$$\text{E-CELL: } \tfrac{1}{2}O_2(\text{Air}) \rightarrow \tfrac{1}{2}O_2 - \text{energy} \tag{6}$$

$$\text{DEVICE: } O_2(\text{Air}) + Zn \rightarrow ZnO + \tfrac{1}{2}O_2$$

There are of course other electrochemical reactions which will generate gases such as hydrogen which can serve to move the liquid through the device. Electrolysis of water can yield either hydrogen or oxygen, as can galvanic cells using metal oxides such as oxides of zinc, nickel, lead and similar metals. A typical example of such a cell is disclosed in U.S. Pat. No. 5,242,565 (Winsel). While air, oxygen and hydrogen are the gases most commonly available by conventional electrochemical reactions, the invention is not intended to be limited only to those three. Rather it is also applicable to any gas which 1) can be generated by an electrochemical reaction cell which is similar in function and size to the oxygen cell exemplified in this Specification, 2) is inert or substantially non-reactive with the liquid which it is intended to move through the device of this invention, and 3) is inert to the ambient environment surrounding the device and to the users of the device, in that its generation and dispersion does not also involve the use or generation of toxic, hazardous, reactive or incompatible materials in conjunction with the generation of the subject gas.

In the illustrated embodiment of the invention, the electrochemically active material which is reduced by the electrochemical cell 92 is also the activating agent for the battery 76, namely, the atmospheric oxygen entering the ports 106. The oxygen reaches the cell 92 by passing through cavities or passageways in the zone 113 which by-pass the core 98. It will be appreciated, however, that separate air inlet ports or other means may be provided for supplying atmospheric oxygen to the cell 92 independently of the supply to the battery 76. Moreover, it will also be appreciated that in certain applications it may be necessary or desirable to use an electrochemically active material differing from the battery activating agent, in which case separate inlet ports or other types of inlet arrangements may be required. It will also be appreciated that reactions 3 and 4 can also be achieved by using batteries, such as silver oxide batteries, which do not require oxygen for activation. In this case, the air inlet ports need only to provide air to the electrochemical cell cathode.

It will be seen that the gas/liquid interface 20 clearly operates on a very small portion of the overall surface area of the fluid contained in the elongated conduit 8. As will be seen from the examples below, for commonly used sizes of the present device containing spiral, helical or circular conduit patterns, the ratio of the surface area of the gas/liquid interface to the entire surface area of the liquid (when the device is substantially full at the beginning of its use) will normally be on the order of 1:200 or greater. Commonly it will be in the range of 1:1000 or greater, preferably up to on the order of 1:10,000. It will thus be seen that a unique and important feature of the present invention is the fact that the motive power of the pump-motivated gas is throughout most of the operational life of the device exerted only against a very small fraction of the surface area of the liquid.

Typical liquid flow rates of the present devices are illustrated in Examples 1–3 below. The examples are derived from tests utilizing a device of the type shown in FIGS. 1 and 2 where the reservoir conduit 8 was composed of Tygon™ tubing in a spiral coil. The tubing had a 0.050 in. (1.27 mm) inside diameter and 0.090 in. (2.29 mm) outside diameter (known as "50/90" tubing) and was driven by a conventional silver oxide battery having a voltage of 1.35–1.45V and available commercially under the trade name Eveready™ as Type 312E.

EXAMPLE 1

In this test, the tubing coil was 2 ft. (61 cm) long, the resistor value was 25,000Ω, the fluid was water and there was a 2 mm oil slug placed between the gas and water phases. The device delivered the fluid at a flow rate of about 3.3–3.4 $\mu$L per hour (2.45–2.52 mL/month) at 100 hours.

EXAMPLE 2

The data of Example 2 were obtained in the same manner as in Example 1, except that the tubing coil was 1 ft. (30 cm) long. The device delivered the fluid at a flow rate of about 3.4 $\mu$L per hour (2.52 mL/month) after 90 hours.

EXAMPLE 3

The data of Example 3 were obtained in the same manner as for Example 1, except that the resistor value was 19,500Ω. The device delivered the fluid at a flow rate of about 4.4 $\mu$L per hour (3.17 mL/month) after 94 hours.

It will be evident from the above that the devices of this invention are quite useful not only for dispensing medications transdermally to a human or animal patient, but also to dispensing chemicals, vapor forming liquids and their resulting vapors, air freshening devices and dispensing of other liquids to deal with specific problems, such as topical liquids to kill parasites on the surface of a human or animal patient or insecticide vapors. The device can also be used for dispensing such materials as human or animal hormones, birth control compositions, antibiotics and many other useful medications and treatment liquids. The devices can be housed in compact but rugged housings which will stand up to the active movements of people or animals, or in less rugged but more decorative housings which can be used and displayed in homes, offices and other living or working areas. Since the only electrical components are the battery and pump circuitry, and those can be completely enclosed in a sealed or sealable housing as shown in the Figures, the entire device can be made weather and environment resistant, so that, for instance, the device can be used for delivering veterinary medications to horses, cattle or other active animals which commonly remain out of doors in inclement weather.

The devices of this invention are quite compact and readily portable. Typically, including the small battery, a device of the type shown in FIG. 1 or FIG. 6 will have an overall external size not exceeding about 2 in. (5 cm) in diameter and approximately 1 in. (2.5 cm) or less in thickness.

It is evident that there will be numerous embodiments of this invention which, while not expressly described above, are clearly within the scope and spirit of the invention. The above description is therefore intended to be exemplary only, and the actual scope of the invention is to be determined solely from the appended claims.

I claim:

1. A self-contained liquid containment and dispensing device which comprises:

an elongated fluid conduit having a first end and a second end and an internal volume sufficient to contain a predetermined quantity of liquid;

a liquid dispenser in fluid communication with said first end of said conduit, comprising a porous liquid- and gas-permeable material containment member disposed such that said liquid upon discharge from said first end of said conduit flows through said material containment member before exiting from said device, and said member has an internal structure through which said liquid diffuses slowly;

a gas generation member in fluid communication with said second end of said conduit for generating gas and pumping said gas into said conduit through said second end; and an activation circuit comprising an electric power source for electrically activating said gas generation member;

whereby when liquid is contained in said conduit and said gas generation member is activated to generate and pump said gas into said second end of said conduit, said pumped gas forces said liquid to be expelled from said conduit through said first end and dispensed though said dispenser.

2. A device as in claim 1 wherein said fluid conduit is disposed in a spiral or helical configuration.

3. A device as in claim 2 wherein said fluid conduit comprises a length of tubing disposed in a spiral or helical configuration.

4. A device as in claim 1 wherein said fluid conduit comprises a plurality of concentric fluid channels with a fluid passage between each pair of adjacent concentric channels, such that fluid can flow in a continuous path between the outermost and innermost of said channels.

5. A device as in claim 4 wherein said concentric channels are generally circular in plan.

6. A device as in claim 1 wherein said fluid conduit is of sufficient length to hold at least one quantity of each of a plurality of different liquids, said quantities disposed sequentially along the length of said conduit and remaining substantially unmixed at the interfaces between respective adjacent quantities, such that movement of cumulative body of liquids causes each successive different liquid to be expelled seriatim through said first end of said conduit.

7. A device as in claim 6 wherein adjacent quantities of said different liquids are separated by a quantity of a barrier fluid disposed therebetween which is substantially immiscible with either of said adjacent liquids.

8. A device as in claim 1 wherein said liquid is volatile and said material containment member operates to retard the flow of said liquid for a period of time sufficient to permit said volatile liquid to vaporize and said vapor to be dispersed into the ambient environment.

9. A device as in claim 1 wherein said material containment member comprises at least one internal containment site for retaining a material soluble in said liquid, such that the retarded flow of said liquid through said member provides sufficient time for said liquid to at least partially dissolve said soluble material and transport the dissolved material out of said member.

10. A device as in claim 9 wherein said material containment member comprises a body having an internal matrix of interstices, said interstices comprising internal containment sites.

11. A device as in claim 1 further comprising chemical or physical attachment means for attaching said device to another object.

12. A device as in claim 1 further comprising a housing in which said fluid conduit is disposed.

13. A device as in claim 12 wherein said housing is at least partially formed of a transparent material such that the progress of said liquid through said conduit can be observed visually from outside said housing.

14. A device as in claim 12 further comprising said gas generation member and said activation circuit being disposed in a module separable from said housing, said housing containing a receptacle for receiving said module, and upon receiving of said module in said receptacle, said gas generation member and said second end of said liquid conduit become operably connected.

15. A device as in claim 14 further comprising access means in said module for providing access to components of said gas generation member or said activation circuit within said module from the exterior of said module.

16. A device as in claim 1 wherein said gas generation member operates to generate a gas which is substantially unreactive with said liquid and substantially harmless to the ambient environment surround said device and to users of said device.

17. A device as in claim 1 wherein said gas generation member operates to generate gaseous air, oxygen or hydrogen.

18. A device as in claim 1 wherein said dispensing device comprises administration means for administering said liquid to a human or animal.

19. A device as in claim 18 wherein said dispensing device comprises administration means to administer said liquid transdermally or topically.

20. A device as in claim 1 wherein said liquid is volatile and dispensing device comprises means for retaining said liquid during volatilization and dispersing vapor so formed to ambient environment.

21. A method of administering a liquid to a human or animal patient which comprises:

a. providing a self-contained liquid containment and dispensing device which comprises:

i. an elongated fluid conduit having a first end and a second end and an internal volume sufficient to contain a predetermined quantity of liquid;

ii. a liquid dispenser in fluid communication with said first end of said conduit, comprising a porous liquid- and gas-permeable material containment member disposed such that said liquid upon discharge from said first end of said conduit flows through said material containment member before exiting from said device, and said member has an internal structure through which said liquid diffuses slowly;

iii. a gas generation member in fluid communication with said second end of said conduit for generating and pumping gas into said conduit through said second end; and iv. an activation circuit comprising an electric power source for electrically activating said gas generation member;

b. placing a quantity of said liquid within said conduit;

c. attaching said device to said patient in such manner that said liquid dispenser is in fluid communication with said patient; and d. activating said circuit to operate said gas generation member to generate and pump said gas into said second end of said conduit, said pumped gas forcing said liquid to be expelled from said conduit through said first end and administered though said dispenser to said patient.

22. A method as in claim 21 wherein said liquid dispenser comprises a skin contact pad and said administration is transdermal or topical.

23. A method as in claim 22 wherein said skin contact pad comprises at least one internal containment site for retaining a material soluble in said liquid, such that the retarded flow of said liquid through said pad provides sufficient time for said liquid to at least partially dissolve said soluble material and transport the dissolved material out of said pad.

24. A method as in claim 23 wherein said pad comprises an internal matrix of interstices, said interstices comprising said internal containment sites.

25. A method as in claim 23 wherein said material soluble in said liquid administered comprises a medication, a hormone, a drug, a treating agent for a disease or dysfunction, a vitamin, a mineral, a dietary supplement or a biological composition and said material following dissolution in said liquid during passage of said liquid through said pad is administered to said patient simultaneously with administration of said liquid.

26. A method as in claim 21 wherein said device is attached to said patient by adhesive.

27. A method as in claim 21 further comprising placing a quantity of each of a plurality of different liquids into said conduit with said quantities disposed sequentially along the length of said conduit and remaining substantially unmixed at the interfaces between respective adjacent quantities, said activation thereupon causing each successive different liquid to be expelled seriatim through said first end of said conduit.

28. A method as in claim 27 wherein each said liquid administered comprises a medication, a hormone, a drug, a treating agent for a disease or dysfunction, a vitamin, a mineral, a dietary supplement or a biological composition, and at least two of said liquids differ from each other.

29. A method as in claim 21 wherein said liquid is administered to a human patient.

30. A method as in claim 21 wherein said liquid is administered to a veterinary patient.

31. A method of delivering a vaporized liquid to the ambient environment which comprises:

a. providing a self-contained liquid containment and dispensing device which comprises:
   i. an elongated fluid conduit having a first end and a second end and an internal volume sufficient to contain a predetermined quantity of liquid;
   ii. a liquid dispenser in fluid communication with said first end of said conduit, comprising a porous liquid- and gas-permeable material containment member disposed such that said liquid upon discharge from said first end of said conduit flows through said material containment member before exiting from said device, and said member has an internal structure through which said liquid diffuses slowly;
   iii. a gas generation member in fluid communication with said second end of said conduit for pumping gas into said conduit through said second end; and
   iv. an activation circuit comprising an electric power source for electrically activating said gas generation member;

b. placing a quantity of volatile liquid within said conduit;

c. placing said device containing said volatile liquid within said ambient environment; and d. activating said circuit to operate said gas generation member to pump said gas into said second end of said conduit, said pumped gas forcing said liquid to be expelled from said conduit through said first end;

e. retaining at least a portion of said volatile liquid within said device for a period of time sufficient for said portion to vaporize; and f. dispersing the resultant vapor through said dispenser into said ambient environment.

32. A method as in claim 31 wherein said vapor emits a fragrance within said ambient environment.

33. A method as in claim 31 wherein said vapor contains a compound which masks or eliminates undesirable odors in said ambient environment.

34. A method as in claim 31 wherein said vapor contains an insecticidal chemical.

35. A method as in claim 34 wherein said vapor further contains an insect attractant chemical or pheromone.

36. A method as in claim 31 further comprising disposing said device within a decorative housing.

37. A method as in claim 31 further comprising placing a quantity of each of a plurality of different vaporizable liquids into said conduit with said quantities disposed sequentially along the length of said conduit and remaining substantially unmixed at the interfaces between respective adjacent quantities, said activation thereupon causing each successive different vaporizable liquid to be expelled seriatim through said first end of said conduit and vapors therefrom being dispersed seriatim to the ambient environment.

* * * * *